(12) United States Patent
Li et al.

(10) Patent No.: US 6,861,413 B2
(45) Date of Patent: Mar. 1, 2005

(54) STABLE NON-DIHYDRATE AZITHROMYCIN ORAL SUSPENSIONS

(75) Inventors: Zheng J. Li, Quaker Hill, CT (US); Andrew V. Trask, Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/621,226

(22) Filed: Jul. 15, 2003

(65) Prior Publication Data

US 2004/0121966 A1 Jun. 24, 2004

Related U.S. Application Data

(63) Continuation-in-part of application No. 10/152,106, filed on May 21, 2002.
(60) Provisional application No. 60/343,041, filed on Dec. 21, 2001, provisional application No. 60/297,741, filed on Jun. 12, 2001, and provisional application No. 60/292,565, filed on May 22, 2001.

(51) Int. Cl.[7] .............................................. A61K 31/70
(52) U.S. Cl. ........................... 514/29; 536/7.4; 424/489
(58) Field of Search ........................... 536/7.4; 514/29; 424/489

(56) References Cited

U.S. PATENT DOCUMENTS

| | | | | |
|---|---|---|---|---|
| 4,328,334 A | 5/1982 | Kobrehel et al. | ............ | 536/7.4 |
| 4,465,674 A | 8/1984 | Bright et al. | ................ | 424/180 |
| 4,474,768 A | 10/1984 | Bright | ......................... | 424/180 |
| 4,517,359 A | 5/1985 | Kobrehel et al. | ............ | 536/7.4 |
| 4,963,531 A | 10/1990 | Remington | .................. | 514/29 |
| 6,245,903 B1 | 6/2001 | Karimian et al. | ............ | 536/7.4 |
| 6,268,489 B1 | 7/2001 | Allen et al. | ................... | 536/7.4 |
| 6,365,574 B2 | 4/2002 | Singer et al. | ................. | 514/29 |
| 6,420,537 B1 | 7/2002 | Bosch et al. | ................. | 536/7.4 |
| 6,451,990 B1 | 9/2002 | Jasanada et al. | ............. | 536/7.4 |
| 6,528,492 B1 | 3/2003 | de la Torre Garcia et al. | ............. | 514/29 |
| 2001/0047089 A1 | 11/2001 | Aronhime et al. | | |
| 2002/0111318 A1 | 8/2002 | Rengaraju | | |

FOREIGN PATENT DOCUMENTS

| | | | | |
|---|---|---|---|---|
| CA | 2245398 | 2/1998 | .......... | C07H/17/00 |
| CN | 1093370 | 12/1994 | .......... | C07H/17/08 |
| CN | 1114960 | 1/1996 | .......... | C07H/17/08 |
| CN | 1161971 | 10/1997 | .......... | C07H/17/08 |
| EP | 0298650 | 6/1988 | .......... | C07H/17/02 |
| EP | 0941999 | 9/1999 | .......... | C07H/17/08 |
| EP | 1103558 | 2/2000 | .......... | C07H/17/08 |
| EP | 1103558 | 5/2001 | .......... | C07H/17/08 |
| EP | 1234833 | 8/2002 | .......... | C07H/17/08 |
| WO | WO9804574 | 2/1998 | .......... | C07H/17/08 |
| WO | WO0014099 | 3/2000 | .......... | C07H/17/08 |
| WO | WO0032203 | 6/2000 | .......... | A61K/31/70 |
| WO | WO0100640 | 1/2001 | .......... | C07H/17/08 |
| WO | WO0149697 | 7/2001 | ............ | C07H/1/00 |
| WO | WO0187912 | 11/2001 | .......... | C07H/17/08 |
| WO | WO0207736 | 1/2002 | ....... | A61K/31/7048 |
| WO | WO0209640 | 2/2002 | | |
| WO | WO0210181 | 2/2002 | .......... | C07H/17/08 |
| WO | WO0215842 | 2/2002 | | |
| WO | WO0242315 | 5/2002 | .......... | C07H/17/08 |
| WO | WO02085898 | 10/2002 | ......... | C07D/413/14 |
| WO | WO0187912 | 11/2002 | .......... | C07H/17/08 |
| WO | WO032922 | 4/2003 | | |

OTHER PUBLICATIONS

Chemical Abstracts, vol. 124, No. 3 (Jan. 15, 1996) Abstract No. 29525, Abstract of CN1093370.

*Primary Examiner*—Elli Peselev
(74) *Attorney, Agent, or Firm*—Peter C. Richardson; Gregg C. Benson; Lance Y. Liu

(57) ABSTRACT

This invention relates to a powder for oral suspension, and an oral suspension made therefrom, which comprises a n-propanol solvate of non-dihydrate azithromycin and an azithromycin conversion stabilizing excipient, wherein said excipient reduces the conversion of the form of azithromycin, when placed in suspension, to another form of azithromycin.

This invention also relates to an oral suspension which comprises a n-propanol solvate of non-dihydrate azithromycin and an aqueous vehicle.

4 Claims, No Drawings

STABLE NON-DIHYDRATE AZITHROMYCIN ORAL SUSPENSIONS

RELATED APPLICATIONS

This application is a continuation-in-part of U.S. Ser. No. 10/152,106, filed May 21, 2002, which is a non provisional of Provisional Applications 60/343,041, filed Dec. 21, 2001, 60/297,741, filed Jun. 12, 2001, and 60/292,565, filed May 22, 2001.

BACKGROUND OF THE INVENTION

Azithromycin, which is also named 9-deoxo-9a-aza-9a-methyl-9a-homoerythromycin A, exists in a dihydrate form as well as in numerous non-dihydrate forms.

Azithromycin is administered for the treatment of various infections, particularly infections of the urinary tract, bronchial tract, lungs, sinuses and the middle ear.

In treating pediatric patients, azithromycin is administered in the dosage form of an oral suspension which is administered through a single or multiple dose course of therapy. The oral suspension dosage form is preferred for pediatric therapeutic use, as it provides better control of the amount of azithromycin administered and as many pediatric patients cannot swallow other oral dosage forms. However, due to azithromycin's extremely bitter taste, suitable flavoring is required to ensure patient compliance and to reduce emesis after swallowing. To date, the oral suspensions of azithromycin comprise azithromycin dihydrate and a combination of banana, cherry and vanilla flavorings which are used to mask the bitter taste of the azithromycin.

Presently, the use of non-dihydrate azithromycin oral suspensions is contemplated. Non-dihydrate azithromycin also has an extremely bitter taste. Due to this bitter taste, these non-dihydrate azithromycin oral suspensions will also require suitable flavoring or sweetening agents to mask the bitter taste and ensure patient compliance. Unfortunately, forms of non-dihydrate azithromycin, when in many flavored oral suspensions, are not stable and often rapidly convert to other forms of azithromycin. No conversion is exhibited by azithromycin dihydrate in flavored oral suspensions.

Conversion from one form of azithromycin to another is undesirable as the subsequent azithromycin forms may not be bioequivalent to the initial azithromycin form. This potential change in bioequivalence, due to azithromycin form conversion, could result in administering an underdose or overdose of azithromycin to a patient, which is particularly significant for pediatric patients who require tighter dosing regimens.

Thus, as form conversion is not a desirable characteristic of a pharmaceutical formulation, what is needed is a means for stabilizing non-dihydrate azithromycin in an oral suspension to reduce the rate of form conversion.

SUMMARY OF THE INVENTION

This invention relates to a powder for oral suspension, and an oral suspension made therefrom, which comprises a n-propanol solvate of non-dihydrate azithromycin and an azithromycin conversion stabilizing excipient, wherein said excipient reduces the conversion of the form of azithromycin, when placed in suspension, to another form of azithromycin.

This invention also relates to an oral suspension which comprises a n-propanol solvate of non-dihydrate azithromycin and an aqueous vehicle.

DETAILED DESCRIPTION

Many forms of non-dihydrate azithromycin, when placed in suspension in an aqueous vehicle, convert to different forms of azithromycin. As used herein, form conversion is defined as the conversion from a first form of non-dihydrate azithromycin into one or more different non-dihydrate forms of azithromycin and/or to azithromycin dihydrate. For example, as shown in the following Example 1, bulk non-dihydrate form G azithromycin experienced significant form conversion when suspended in deionized water.

Further, as shown in Examples 1, 2 and 3, the rate of form conversion, of many non-dihydrate forms of azithromycin, increases significantly if the suspension also contains a conversion enhancer, such as a flavoring, or a component of a flavoring.

The present invention relates to oral suspensions of non-dihydrate azithromycin wherein the rate of conversion of the non-dihydrate azithromycin form has been significantly reduced by the addition of at least one conversion stabilizing excipient. The oral suspensions of the present invention are constituted using powders for oral suspension, of the present invention, and suitable aqueous vehicles.

In this oral suspension, the non-dihydrate azithromycin may be (a) completely suspended in the vehicle or (b) partially suspended in the vehicle and partially in solution in the vehicle. An oral suspension, of the present invention, further includes aqueous vehicles containing azithromycin which is suspended within the vehicle, or wherein the azithromycin is temporarily suspended, in the vehicle after shaking, stirring or mixing.

In the present invention, an oral suspension is a single dose or multi-day dosage form of non-dihydrate azithromycin, for oral administration, that is prepared by mixing a powder for oral suspension, of the present invention, with a suitable aqueous vehicle. A powder for oral suspension (hereinafter "POS"), of the present invention, comprises non-dihydrate azithromycin and a conversion stabilizing excipient.

As used herein, "non-dihydrate azithromycin" means all amorphous and crystalline forms of azithromycin including all polymorphs, isomorphs, clathrates, salts, solvates and hydrates of azithromycin other than form A, the dihydrate form of azithromycin (azithromycin dihydrate).

The non-dihydrate azithromycin used, in the present invention, may be in the form of a powder, or of azithromycin granules, or agglomerated azithromycin particles, which were previously formed from a non-dihydrate azithromycin powder and, optionally, at least one pharmaceutically acceptable excipient.

Non-dihydrate azithromycin includes a hygroscopic hydrate of azithromycin, as disclosed in U.S. Pat. No. 4,474,768, which is designated herein as "form B".

Preferably, the non-dihydrate azithromycin is present in one of several alternate crystalline forms, including forms D, E, F, G, H, J, M, N, O, P, Q and R, which are disclosed in U.S. patent application Ser. No. 10/152,106, filed 21 May 2002, titled "Crystal Forms of Azithromycin", or a mixture of two or more of said crystalline forms.

More preferably, the non-dihydrate azithromycin is an ethanol solvate of azithromycin or an isopropanol solvate of azithromycin. Examples of such ethanol and isopropanol solvates of azithromycin are disclosed in U.S. Pat. No. 6,365,574, by Singer et al., titled "Ethanolate of azithromycin, process for manufacture, and pharmaceutical compositions thereof", U.S. Pat. No. 6,245,903, by Karimian et al., titled "Azithromycin monohydrate isopropanol clatharate and methods for the manufacture thereof" or in U.S. Ser. No. 10/152,106.

The teachings of U.S. Pat. No. 6,365,574, U.S. Pat. No. 6,245,903 and U.S. Ser. No. 10/152,106 are incorporated herein, by reference, in their entirety.

Both Family I and Family II isomorphs are hydrates and/or solvates of azithromycin. The solvent molecules in the cavities have a tendency to exchange between solvent and water under specific conditions. Therefore, the solvent/water content of the isomorphs may vary to a certain extent. Forms B, F, G, H, J, M, N, O, and P belong to Family I azithromycin and belong to a monoclinic $P2_1$ space group with cell dimensions of a=16.3±0.3 Å, b=16.2±0.3 Å, c=18.4±0.3 Å and beta=109±2°.

Form F azithromycin is an azithromycin ethanol solvate of the formula $C_{38}H_{72}N_2O_{12}.H_2O.0.5C_2H_5OH$ in the single crystal structure, specifically, being an azithromycin monohydrate hemi-ethanol solvate. Form F is further characterized as containing 2–5% water and 1–4% ethanol by weight in powder samples. The single crystal of form F is crystallized in a monoclinic space group, $P2_1$ with the asymmetric unit containing two azithromycin, two waters, and one ethanol, as a monohydrate/hemi-ethanolate. It is isomorphic to all Family I azithromycin crystalline forms. The theoretical water and ethanol contents are 2.3 and 2.9%, respectively.

Form G azithromycin is of the formula $C_{38}H_{72}N_2O_{12}.1.5H_2O$ in the single crystal structure, being azithromycin sesquihydrate. Form G is further characterized as containing 2.5–6% water and <1% organic solvent(s) by weight in powder samples. The single crystal structure of form G consists of two azithromycin molecules and three water molecules per asymmetric unit. This corresponds to a sesquihydrate with a theoretical water content of 3.5%. The water content of powder samples of form G ranges from about 2.5 to about 6%. The total residual organic solvent is less than 1% of the corresponding solvent used for crystallization.

Form H azithromycin is of the formula $C_{38}H_{72}N_2O_{12}.H_2O.0.5C_3H_8O_2$ being azithromycin monohydrate hemi-1,2 propanediol solvate. Form H is a monohydrate/hemi-propylene glycol solvate of azithromycin free base.

Form J azithromycin is of the formula $C_{38}H_{72}N_2O_{12}.H_2O.0.5C_3H_7OH$ in the single crystal structure, being azithromycin monohydrate hemi-n-propanol solvate. Form J is further characterized as containing 2–5% water and 1–5% n-propanol by weight in powder samples. The calculated solvent content is about 3.8% n-propanol and about 2.3% water.

Form M azithromycin is an isopropanol solvate of azithromycin of the formula $C_{38}H_{72}N_2O_{12}.H_2O.0.5C_3H_7OH$, specifically, being azithromycin monohydrate hemi-isopropanol solvate. Form M is further characterized as containing 2–5% water and 1–4% 2-propanol by weight in powder samples. The single crystal structure of form M would be a monohydrate/hemi-isopropranolate.

Form N azithromycin is a mixture of isomorphs of Family I. The mixture may contain variable percentages of isomorphs F, G, H, J, M and others, and variable amounts of water and organic solvents, such as ethanol, isopropanol, n-propanol, propylene glycol, acetone, acetonitrile, butanol, pentanol, etc. The weight percent of water can range from 1–5.3% and the total weight percent of organic solvents can be 2–5% with each solvent content of 0.5 to 4%.

Form O azithromycin is of the formula $C_{38}H_{72}N_2O_{12}.0.5H_2O.0.5C_4H_9OH$, being a hemihydrate hemi-n-butanol solvate of azithromycin free base by single crystal structural data.

Form P azithromycin is of the formula $C_{38}H_{72}N_2O_{12}.H_2O.0.5C_5H_{12}O$ being azithromycin monohydrate hemi-n-pentanol solvate.

Form Q azithromycin is of the formula $C_{38}H_{72}N_2O_{12}.H_2O.0.5C_4H_8O$ being azi,thromycin monohydrate hemi-tetrahydrofuran solvate. It contains about 4% water and about 4.5% THF.

Forms D, E and R belong to Family II azithromycin and belong to an orthorhombic $P2_1\,2_1 2_1$ space group with cell dimensions of a=8.9±0.4 Å, b=12.3±0.5 Å and c=45.8±0.5 Å. Form Q is distinct from Families I and II.

Form D azithromycin is of the formula $C_{38}H_{72}N_2O_{12}.H_2O.C_6H_{12}$ in its single crystal structure, being azithromycin monohydrate monocyclohexane solvate. Form D is further characterized as containing 2–6% water and 3–12% cyclohexane by weight in powder samples. From single crystal data, the calculated water and cyclohexane content of form D is 2.1 and 9.9%, respectively.

Form E azithromycin is of the formula $C_{38}H_{72}N_2O_{12}.H_2O.C_4H_8O$ being azithromycin monohydrate mono-tetrahydrofuran solvate. Form E is a monohydrate and mono-THF solvate by single crystal analysis.

Form R azithromycin is of the formula $C_{38}H_{72}N_2O_{12}.H_2O.C_5H_{12}O$ being azithromycin monohydrate mono-methyl tert-butyl ether solvate. Form R has a theoretical water content of 2.1 weight % and a theoretical methyl tert-butyl ether content of 10.3 weight %.

"Bulk azithromycin", as used herein, means azithromycin particles without added excipients. In the present invention, bulk azithromycin may be milled or unmilled.

A conversion enhancer, of the present invention, is a substance which, when included in a suspension comprising non-dihydrate azithromycin and water, increases the rate of conversion of the non-dihydrate azithromycin form, in the suspension, to other forms of azithromycin. Typical conversion enhancers include flavorings, or components thereof such as volatile organic components of the flavoring (e.g. 3-methyl-butyl acetate or isoamyl isovalerate), and viscosifying agents in combination with one or more conversion enhancers, such as flavorings that independently promote conversion.

A conversion stabilizing excipient, of the present invention, is a pharmaceutically acceptable excipient which, when included in a suspension of non-dihydrate azithromycin, significantly reduces the rate of conversion of the non-dihydrate azithromycin form, in the suspension, to other forms of azithromycin.

The term "pharmaceutically acceptable", as used herein, means that which is generally safe, non-toxic and neither biologically nor otherwise undesirable and includes that which are acceptable for human pharmaceutical use as well as veterinary use. In the present invention, the excipients and aqueous vehicle are pharmaceutically acceptable.

An aqueous vehicle, of the present invention, comprises unflavored water, flavored water, or a natural or artificial fruit, or otherwise flavored, aqueous solution such as a beverage.

In one embodiment of the present invention the oral suspension, and the POS of the present invention from which it is made, do not include a conversion enhancer, such as a flavoring. Thus, neither the POS nor the aqueous vehicle is flavored. In this embodiment, a suitable conversion stabilizing excipient is a viscosifying agent. Preferably, the amount of viscosifying agent contained in the POS is sufficient to raise the viscosity of the oral suspension to about 3 centipoise or more. More preferably, the viscosity of the oral suspension is about 40 centipoise or more. Suitable viscosifying agents include pharmaceutically acceptable excipients that are chemically inert towards non-dihydrate azithromycin and that increase the viscosity of the oral suspension. Such viscosifying agents include, for example, sugars, such as sucrose, glucose, maltose dextrose and fructose, hydric alcohols, such as sorbitol, mannitol, xylitol and maltitol, and polymers such as polydextrose, xanthan gum, guar gum, sodium alginate, carrageenan, hydroxypropyl cellulose (HPC), hydroxypropyl methylcellulose (HPMC), methylcellulose, polyvinylpyrrolidone (PVP), maltodextrin, carbomer, polyvinyl alcohol, polyethylene glycol (PEG), polyethylene oxide, carboxymethylcellulose (CMC) and hydroxyethyl cellulose (HEC).

In the present invention, it is preferred that the bitter taste of azithromycin, in an oral suspension, is masked by including a flavoring or a combination of flavorings. Flavorings incorporated in the composition may be chosen from synthetic flavor oils and flavoring aromatics and/or natural oils, extracts from plants, leaves, flowers, fruits, and so forth and combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth. The amount of flavoring may depend on a number of factors including the organoleptic effect desired. Generally the flavoring will be present in an amount of from 0.002 to about 3.0 percent weight per volume of the constituted suspension.

Preferred flavorings are those which provide a constant flavor for approximately 5 days at the elevated pH of the formulation after constitution. More preferably, the flavoring is selected from the group consisting of vanilla, grape, cherry, banana, and mixtures thereof. An even more preferred flavoring comprises a combination of cherry and banana. Said preferred flavoring may further comprise creme de vanilla. Such flavors are available commercially from Bush Boake Allen, Inc., Chicago, Ill.

In the present invention, flavorings do not include sweetening with a sugar or an artificial sweetener.

In a preferred embodiment of the present invention, an oral suspension containing a conversion enhancer, such as a flavoring, and the POS of the present invention from which it is made, include at least one surface tension reducing excipient. Suitable surface tension reducing excipients include, for example, anionic surfactants, nonionic surfactants, surface active polymers and combinations thereof. Preferred surface tension reducing excipients are those which reduce the surface tension of water by greater than about 20 dynes/cm. Since the surface tension of water is around 70 dynes/cm, preferred surface tension reducing excipients reduce the surface tension of water to below around 50 dynes/cm. More preferred surface tension reducing excipients reduce the surface tension of water to below around 40 dyne/cm.

Examples of preferred anionic surfactants are sodium lauryl sulfate, sodium dioctyl sulfosuccinate, and bile salts such as sodium taurodeoxycholate. Other anionic surfactants are described in "Surfactants and Interfacial Phenomena", M. J. Rosen, John Wiley and Sons, N.Y., 1978.

Examples of preferred non-ionic surfactants are polysorbates such as polyoxyethylene sorbitan monostearate (Tween 60) and polyoxyethylene sorbitan monooleate (Tween 80), and nonylphenoxypolyoxyethylenes (NPPOEs) with average polyoxyethylene repeat numbers of 9, 10.5, 20, 30, 50, and 100. NPPOE-9, -10.5, -20, -30, -50, and -100 are sold under the brand names Igepal® CO-630, -710, -850, -880, -970, and -990, respectively.

Also preferred are polyoxyethylene ethers (e.g Brijo series), for which the alkyl chain length and polyoxyethylene repeat number may vary. Examples are C12/POE9, C16/POE9, C18/POE9, C12/POE25, and the like. Also preferred are nonionic surfactants of the Triton® series, e.g. octylphenol ethylene oxide condensate (Triton® X-100). It will be appreciated by those familiar with the art that there are many types of non-ionic surfactants, as discussed for example in "Nonionic Surfactants", M. Schick, ed., Marcel Dekker, N.Y., 1967, and in "Surfactants and Interfacial Phenomena", M. J. Rosen, John Wiley and Sons, N.Y., 1978.

It is well known that addition of an anionic or non-ionic surfactant to water results in a relatively linear decrease in surface tension as the surfactant concentration is increased, until the surfactant's critical micellar concentration (CMC) is reached. Above the CMC, as further surfactant is added, there is minimal or no further decrease in surface tension. For the current invention, an amount of solid surfactant must be added to the POS which is sufficient to lower the surface tension of the amount of water or other aqueous vehicle which will be mixed with the POS to constitute the therapeutic suspension which the patient will consume. For example, if the POS is intended for 5-day therapy and contains 1 gm azithromycin (200 mg per daily dose), and if the daily dose is to be reconstituted in 2 ml water, then the POS would be reconstituted with 10 ml water, and a preferred amount of non-ionic surfactant must be included in the POS which will lower the surface tension of 10 ml water by about 20 dynes/cm or more.

Preferred quantities of anionic or non-ionic surfactants in POS formulations are those quantities which will lower the surface tension of the reconstitution liquid, at the volume used for reconstitution, to below around 50 dynes/cm, preferably below around 40 dynes/cm. For example, a 1% w/v (1 gm/100 ml) solution of the NPPOE surfactants named above lowers the surface tension of water below 50 dynes/cm, as does a 1% w/v solution of Tween 80, sodium taurodeoxycholate, or sodium lauryl sulfate. Lower concentrations may also be effective. For example, a 0.01% solution also meets this preferred criterion for NPPOEs from NPPOE-9 to NPPOE-30. A 0.2% w/v sodium lauryl sulfate solution also meets this preferred criterion. In order to minimize any toxicity associated with a surfactant, it is preferred that the amount of surfactant used be the minimum required to lower the surface tension of the reconstitution liquid, at the volume used for reconstitution, to below around 50 dynes/cm, preferably below around 40 dynes/cm. It will be apparent to those familiar with the art that a determination of the minimum amount of surfactant to be used can be made as follows. The surface tension of water is measured using one of a variety of common methods (e.g. Wilhelmy plate method, bubble surface tensiometry) in the presence of increasing amounts of dissolved surfactant, at room temperature, i.e. at around 25 degrees C. The lowest surfactant concentration at which the surface tension is below 50 dynes/cm is the minimum preferred concentration. An amount of surfactant sufficient to achieve this concentration in the reconstituted POS is added to the POS powder formulation.

Examples of surface active polymers include hydroxypropyl methylcellulose, hydroxypropyl methylcellulose acetate succinate, hydroxypropyl cellulose, and polyoxyethylene-polyoxypropylene copolymers (e.g. Pluronic®). Preferred quantities of surface active polymers may be determined utilizing the surface tensiometry methods described above for surfactants.

Therefore, as described above, a POS of the present invention comprises non-dihydrate azithromycin and an azithromycin conversion stabilizing excipient. Preferably, a POS further includes at least one flavoring.

It is also preferred that the POS contain a form of non-dihydrate azithromycin selected from the forms B, D, E, F, G, H, M, N, O, P, Q, R, or mixtures thereof.

More preferably, in the POS of the present invention, the non-dihydrate azithromycin is either an ethanol solvate of azithromycin or an isopropanol solvate of azithromycin.

As a n-propanol solvate of non-dihydrate azithromycin, such as form J of azithromycin, has been found to be most resistant to conversion in a flavored suspension it is the least likely to require a conversion stabilizing excipient. Thus, in an alternate embodiment of the present invention, the POS of the present invention comprises a n-propanol solvate of azithromycin, preferably azithromycin form J, and at least one pharmaceutically acceptable excipient. Further, an alternate oral suspension of the present invention comprises a n-propanol solvate of azithromycin, preferably azithromycin form J, and an aqueous vehicle.

All oral suspensions of the present invention, and the POS from which they are constituted, may optionally include a non-viscosifying sweetener. Suitable non-viscosifying sweeteners include, for example, saccharin, aspartame, acesulfame potassium, thaumatin and monelin.

Other excipients and coloring agents may also be added to the POS of the present invention.

Azithromycin suspensions according to the invention may contain in addition to azithromycin, one or more thickening agents in a total amount of 0.1 to 85% weight per volume in the constituted suspension.

The thickening agent may be the viscosifying agent.

These thickening agents include, for example, sucrose, sorbitol, mannitol, xylitol, maltitol, and polydextrose.

Other suitable thickening agents which function as suspending agents include, for example, hydrocolloid gums and clays known for such purpose, examples of which include xanthan gum, guar gum, locust bean gum, gum tragacanth, acacia, bentonite, magnesium aluminum silicate and the like.

Alternatively, an azithromycin suspension may contain one or more suspending agents such as sodium carboxymethylcellulose, polyvinylpyrrolidone, hydroxypropyl cellulose, hydroxypropyl methylcellulose, methylcellulose, hydroxyethyl cellulose, carbomer, microcrystalline cellulose with sodium carboxymethylcellulose sodium and the like. These suspending agents may also be used in an amount of from 0.3 to 10% weight per volume in the constituted suspension.

POS formulations may also include cyclical oligosaccharides such as cyclodextrins and their derivatives, for example α-cyclodextrin, β-cyclodextrin, γ-cyclodextrin, hydroxypropyl, hydroxyethyl and sulfobutylether cyclodextrin derivitives.

Dispersing agents may also be used in an amount of from 0.05 to 2% weight per volume in the constituted suspension. Dispersing agents include colloidal silicon dioxide, available from Cabot Corporation, Boston, Mass. under the trade designation Cab-O-Sil® and from Degussa AG, Dusseldorf, Germany under the trade designation Aerosil®.

Preservatives may also be used in an amount from 0.01 to 1% weight per volume in the constituted suspension. Suitable preservatives are well known, for example sodium benzoate, methylparaben, propylparaben and the like.

Coloring agents include, but are not limited to, titanium dioxide and/or dyes suitable for food such as those known as F. D. & C, dyes, aluminum lakes and natural coloring agents such as grape skin extract, beet red powder, beta carotene, annato, carmine, turmeric, paprika, and so forth. A coloring agent is an optional ingredient in the compositions of this invention, but when used will generally be present in an amount up to about 2 percent weight per volume in the constituted suspension.

A POS may also contain conventional optional ingredients such as (1) wetting agents, for example, sorbitan monolaurate and polysorbate 80; (2) anti-foaming agents and (3) sweeteners such as glucose, sucrose, fructose, maltose, glycerin, sorbitol, xylitol and mannitol.

Artificial sweeteners may also be used. These include aspartame, sodium saccharin, calcium saccharin, acesulfame potassium, Thaumatin, and monelin. The artificial sweeteners may be used in an amount of from 0.01 to 1% weight per volume in the constituted suspension.

The azithromycin dosage forms of this invention are powders for oral suspension and the oral suspensions themselves. Typically, the powder is a non-caking, free flowing powder which is sold direct to pharmacies or other retail outlets and then made up into the actual suspension by a pharmacist. The oral suspension is, thus, the actual dosage form ingested by patients. The typical shelf life for a constituted suspension is from about 1 to 14 days.

To prepare a powder for oral suspension, the various components may be weighed, delumped and combined.

It is not necessary for the components of the POS to be mixed together prior to constitution with the vehicle. Thus, the POS may be a heterogeneous or a substantially homogeneous mixture of its components.

Preferably, the POS does contain a generally homogeneous mixture of its components. This is particularly important when filling a suspension batch into individual bottles or other packaging such as pouches for sachet dosage forms.

The components of the POS may be combined by blending, mixing, stirring, shaking, tumbling, rolling or by any other methods of combining the POS components. If the POS components are mixed, it is preferable that the azithromycin and excipients are combined under low shear conditions in a suitable apparatus, such as a V-blender, tote blender, double cone blender or any other apparatus capable of functioning under preferred low shear conditions. Preferably, azithromycin and flavorings are blended, and other ingredients are separately blended. Finally, these two blends are blended and deagglomerated.

The invention should not be considered limited to these particular conditions for combining the components and it will be understood, based on this disclosure that the advantageous properties can be achieved through other conditions provided the components retain their basic properties and substantial homogeneity of the components of the POS is otherwise achieved without any significant segregation.

Preferred oral suspensions are those which resuspend easily after constitution with aqueous media and which do not cake on storage after constitution. Preferred suspensions contain sucrose NF, when sucrose is used, and anhydrous excipients when available, to assure facile suspension upon constitution.

In the present invention, the conversion of a form of non-dihydrate azithromycin, contained in an oral suspension, is reduced by including a conversion stabilizing excipient in the oral suspension.

Preferably, the conversion stabilizing excipient is a surface tension reducing excipient. Typically, the surface tension reducing excipient is an anionic surfactant, a non-ionic surfactant or a surface active polymer.

More preferably, the amount of a surface tension reducing excipient, mixed with a volume of aqueous vehicle, to thereby reduce form conversion wherein, is said amount of surface tension reducing excipient which would lower the surface tension of a volume of water, equal to said volume of the aqueous vehicle, to below 50 dynes/cm. Even more preferably, the amount of the surface tension reducing excipient used would reduce the surface tension of the equal volume of water below 40 dynes/cm.

In another embodiment of the present invention, wherein the oral suspension does not contain a conversion enhancer, such as a flavoring, form conversion of non-dihydrate azithromycin in an oral suspension is reduced by including a viscosifying agent in the oral suspension. Preferably, the amount of viscosifying agent used in the oral suspension is sufficient to raise the viscosity of the oral suspension to about 3 centipoise or more. More preferably, the viscosity of the oral suspension is raised to about 40 centipoise or more.

In a further embodiment of the present invention, wherein the oral suspension contains a conversion enhancer, such as a flavoring, form conversion of non-dihydrate azithromycin in an oral suspension is reduced by lowering the viscosity of the oral suspension to about 1 centipoise or less at room temperature.

Typically, viscosity is reduced by using amount and types of excipients that do not significantly raise the viscosity of the aqueous vehicle. For example, instead of using sugar, which increases suspension viscosity, as a sweetener, a non-viscosifying sweetener, such as saccharin, aspartame, acesulfame potassium, thaumatin, and monelin, can be used.

In yet an alternate embodiment of the present invention, the form conversion of non-dihydrate azithromycin in an oral suspension is reduced by administering the oral suspension to the patient within a period of time after constituting so that the level of the azithromycin form conversion is less than 10%. In this embodiment, it is preferred that the conversion enhancer comprises at least one flavoring. More preferably, the oral suspension is administered to the patient within about 1 hour after constitution.

For purposes of this invention, azithromycin may be administered alone or in combination with other therapeutic agents.

Typically, azithromycin is administered in dosage amounts ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. The preferred dosage amount is from about 2 mg/kg/day to about 50 mg/kg/day.

Preferably, the powder for oral suspension is in a dosage form of a single use or multiple use bottle. Most preferred the bottle is a 60 cc high density polyethylene (HDPE) bottle with a child resistant cap. A specified volume of aqueous vehicle is typically added to the bottle containing the powders for oral suspension and shaken to provide a homogeneous constituted suspension.

In another preferred embodiment, the powder for oral suspension is in a dosage form of a unit dose packet (sometimes referred to in the art as a "sachet") which is typically emptied into an aqueous vehicle in preparing an oral suspension. It is noted that powders for oral suspension and unit dose packets, of course, are not ingested directly by patients. Rather, they are constituted in a suitable vehicle. These terms are nonetheless considered to be within the penumbra of the term "dosage form" for purposes of this invention.

A powder for oral suspension typically contains an amount of azithromycin suitable for either single dose administration or for multidose administration over a dose administration period of 1–10 days.

A single dose sachet is designed to be emptied into an aqueous vehicle or alternatively the aqueous vehicle is added to a bottle containing the single dose or multidose powder for oral suspension.

Generally, it is noted that, when a powder for oral suspension is mixed with the aqueous vehicle, the azithromycin contained therein is substantially suspended in the liquid, if constituted according to directions, although the extent of suspension versus solution depends on a number of factors such as pH.

The oral suspensions of the present invention may be used for the treatment of bacterial or protozoal infections. The term "treatment", as used herein, unless otherwise indicated, means the treatment or prevention of a bacterial or protozoal infection, including curing, reducing the symptoms of or slowing the progress of said infection.

As used herein, unless otherwise indicated, the term "bacterial infection(s)" or "protozoal infection(s)" includes bacterial infections and protozoal infections that occur in mammals, fish and birds as well as disorders related to bacterial infections and protozoal infections that may be treated or prevented by administering antibiotics such as the compound of the present invention. Such bacterial infections and protozoal infections and disorders related to such infections include, but are not limited to, the following: pneumonia, otitis media, sinusitis, bronchitis, tonsillitis, and mastoiditis related to infection by *Streptococcus pneumoniae, Haemophilus influenzae, Moraxella catarrhalis, Staphylococcus aureus*, or *Peptostreptococcus* spp.; pharynigitis, rheumatic fever, and *glomerulonephritis* related to infection by *Streptococcus pyogenes*, Groups C and G *streptococci, Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal Groups C–F (minute-colony *streptococci*), *viridans streptococci, Corynebacterium minutissimum, Clostridium* spp., or *Bartonella henselae*; uncomplicated acute urinary tract infections related to infection by *Staphylococcus saprophyticus* or *Enterococcus* spp.; *urethritis* and cervicitis; and sexually transmitted diseases related to infection by *Chlamydia trachomatis, Haemophilus ducreyi, Treponema pallidum, Ureaplasma urealyticum*, or *Neisseria gonorroeae*; toxin diseases related to infection by *S. aureus* (food poisoning and Toxic shock syndrome), or Groups A, B, and C *streptococci*; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis related to infection by *Helicobacter pylori* or *Chlamydia pneumoniae*. Bacterial infections and protozoal infections and disorders related to such infections that may be treated or prevented in animals include, but are not limited to, the following: bovine respiratory disease related to infection by *P. haem., P. multocida, Mycoplasma bovis*, or *Bordetella* spp.; cow enteric disease related to infection by *E. coli* or protozoa (i.e., coccidia, cryptosporidia, etc.); dairy cow mastitis related to infection by Staph. aureus, *Strep. uberis, Strep. agalactiae, Strep. dysgalactiae, Klebsiella* spp., *Corynebacterium*, or *Enterococcus* spp.; swine respiratory disease related to infection by *A. pleuro., P. multocida*, or *Mycoplasma* spp.; swine enteric disease related to infection by *E. coli, Lawsonia intracellularis, Salmonella*, or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by Staph. epidermidis, Staph. intermedius, coagulase neg. Staph. or P. multocida; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas*, or *Prevotella*. Other conditions that may be treated by the compounds and preparations of the present invention include malaria and atherosclerosis. Other bacterial infections and protozoal infections and disorders related to such infections that may be treated or prevented in accord with the method and compositions of the present invention are referred to in J. P. Sanford et al., "The Sanford Guide To Antimicrobial Therapy," 26th Edition, (Antimicrobial Therapy, Inc., 1996).

The term "mammal" is an individual animal that is a member of the taxonomic class Mammalia. The class Mammalia includes, for example, humans, monkeys, chimpanzees, gorillas, cattle, swine, horses, sheep, dogs, cats, mice and rats.

In the present invention, the preferred mammal is a human.

Although the foregoing invention has been described in some detail for purposes of illustration, it will be readily apparent to one skilled in the art that changes and modifications may be made without departing from the scope of the invention described herein.

Exemplification

The present invention will be further illustrated by means of the following examples. It is to be understood, however, that the invention is not meant to be limited to the details described therein.

Excipients, used in the following examples, were obtained as follows: Sucrose (Granulated Sugar) from American Sugar Division, Amstar Corporation (New York, N.Y.); sorbitol (Neosorb®P110) from Roquette America, Inc. (Keokuk, Iowa); Xanthan Gum (Keltrol®) from The Nutrasweet Kelco Company (San Diego, Calif.); Hydroxypropyl Cellulose (Klucel®-EF) Carboxymethylcellulose Sodium 7LF PH from Aqualon Company (Hopewell, Va.); Sodium Phosphate, Tribasic, Anhydrous from FMC Corporation (Carteret, N.J.); FD&C Red #40 Lake Concentrate from Warner-Jenkinson Company (St. Louis, Mo.); Trusil Spray Dried Artificial Cherry Flavor (#11929), Artificial Crème de Vanilla Flavor (#11489), and Trusil Artificial Banana Flavor (#15223) from Bush Boake Allen Inc. (Chicago, Ill.); B&C Banana Concentrate Artificial "K" from Virginia Dare Extract Co., INC. (Brooklyn, N.Y.); Permaseal® Artificial Grape Flavor (Lot#5899019876) from Givaudan Roure Flavors (Cincinnati, Ohio); Hydroxypropyl Methylcellulose Acetate Succinate (AS-MG) from Biddle Sawyer Corporation (New York, N.Y.); Hydroxypropyl Methylcellulose (Methocelo E5 Premium LV) from Dow Chemical Company (Midland, Mich.); Cellulose Acetate Phthalate from Eastman Chemical Company (Kingsport, Tenn.); Polyvinylpyrrolidone (Povidone, Plasdone®) from ISP Technologies (Texas City, Tex.); Sodium Lauryl Sulfate from Aceto Corporation (Flushing, N.Y.); Sodium Dioctyl Sulfosuccinate from Acros Organics (Trenton, N.J.); polyoxyethylene-polyoxypropylene copolymer (poloxamer, Pluronic® F68NF) from BASF Corporation (Mount Olive, N.J.); nonylphenoxy polyoxyethylene (Igepal® CO-630) from Rhodia North American Chemicals (Cranbury, N.J.); 3-Methyl-1-Butanol from Sigma (St. Louis, Mo.); and Ethyl Acetate, Ethyl Ester Propanoic Acid, 3-Methyl-butyl Acetate, 2-Methyl-butyl Acetate, Benzaldehyde and Isoamyl Isovalerate from Aldrich (Milwaukee, Wis.). All water used in the examples is deionized water.

The three powder for oral suspension formulations, used in the examples were as follows:

| Component | Mass (g) |
|---|---|
| Formulation I | |
| Azithromycin | 0.820 |
| Sucrose | 30.600 |
| Sodium Phosphate Tribasic Anhyd. | 0.065 |
| Hydroxypropyl Cellulose | 0.052 |
| Xanthan Gum | 0.052 |
| FD&C Red #40 | 0.001 |
| Formulation II | |
| Azithromycin | 0.820 |
| Sucrose | 30.600 |
| Sodium Phosphate Tribasic Anhyd. | 0.065 |
| Hydroxypropyl Cellulose | 0.052 |
| Xanthan Gum | 0.052 |
| FD&C Red #40 | 0.001 |
| Cherry Flavor | 0.120 |
| Vanilla Flavor | 0.260 |
| Trusil Banana Flavor | 0.200 |
| Formulation III | |
| Azithromycin | 0.820 |
| Sucrose | 30.600 |
| Sodium Phosphate Tribasic Anhyd. | 0.065 |
| Hydroxypropyl Cellulose | 0.052 |
| Xanthan Gum | 0.052 |
| FD&C Red #40 | 0.001 |

-continued

| Component | Mass (g) |
|---|---|
| Cherry Flavor | 0.120 |
| Vanilla Flavor | 0.260 |
| B&C Banana Flavor | 0.200 |

These POS formulations were created by individually weighing each formulation component into a 60-cc High Density Polyethylene (HDPE) bottle with closure. The resulting formulations were then dry-mixed with a Turbula blender (Glen Mills Inc. Maywood, N.J.) for 5 minutes. The powder blends were then constituted with 18 mls of water, shaken for 30 seconds and stored without agitation under controlled temperature conditions.

Upon conclusion of the storage time period the POS samples were filtered using a Buchner funnel in combination with a standard vacuum filtration apparatus. A Millipore prefilter (AP25, 47 mm) was fitted onto the funnel for the collection of suspended solids. Before filtering, the constituted POS sample was poured into a 200 ml volumetric flask and diluted to 200 ml with water. This lowered the viscosity of the sample, facilitating a quick filtration step. With the vacuum on, the diluted POS samples were poured onto the Millipore prefilter. The isolated filtrate remaining on top of the prefilter was then allowed to stand for 2-minutes in order to dry. Vacuum was applied to the filtration apparatus during this drying step. Suspensions containing only bulk drug were transferred directly onto the filter paper upon completion of storage, without the described dilution step during sample preparation. After drying, the collected filtrate was placed into 4 cc Sunbroker vials and analyzed via Solid-State Nuclear Magnetic Resonance (SS-NMR) for quantification of conversion to azithromycin dihydrate (form A).

Approximately 300 mg of sample were tightly packed into a 7 mm ZrO spinner for each sample analyzed. One-dimensional $^{13}$C spectra were collected at ambient pressure using $^{1}$H-$^{13}$C cross-polarization magic angle spinning (CPMAS) at 295 K on a Bruker 7mm BL CPMAS probe positioned into a wide-bore Bruker Avance DSX 500 MHz NMR spectrometer (Bruker BioSpin Corporation; Billerica, Mass.). The samples were spun at 7000 Hz corresponding to the maximum specified spinning speed for the 7 mm spinners. The fast spinning speed minimized the intensities of the spinning side bands. To optimize the signal sensitivity, the cross-polarization contact time was adjusted to 2.3 ms and the decoupling power was set to 65 kHz. Typically, a total of 600 scans were acquired, resulting in approximately a 30 minute acquisition time. The spectra were referenced using an external sample of adamantane with its most upfield resonance set to 29.5 ppm.

Eight pairs of resolved peaks were identified to calibrate ratios of form A in the presence of form G, N, M or F. Integral intensities of all peaks were used as input for the calibration procedure using five different binary mixtures ranging from 3 to 81% of form A with each non-dihydrate form. From this, one non-linear calibration graph was generated for each pair of peaks and each form. For the experimental samples, only the peaks that were totally void from excipient overlap were preferentially integrated. The unknown percentages of form A were then determined from the appropriate calibration graphs. The final result for each sample analyzed was calculated as a weighted average of the determinations from each resolved peak pair.

EXAMPLE 1

Stability of Non-Dihydrate Azithromycin in Water and Flavored Oral Suspensions

The stability of various forms of non-dihydrate azithromycin, in water and in flavored oral suspensions, was evaluated. Specifically, non-dihydrate azithromycin forms G, M, N, F and J were separately used in POS formulation II. These POS formulations were constituted by mixing with 18 mls of water. The suspensions were then stored for 1, 5 and 10 days at either 5° C. or 30° C. Suspensions of bulk azithromycin forms G, M, N, F and J were also constituted with 18 mls of water and stored under the same conditions.

Upon conclusion of the storage time period the suspensions were filtered and suspended solids collected as described previously. These solids were then analyzed by SS-NMR in order to quantify the presence of dihydrate azithromycin (form A), reported as weight percent (% wt), of the recovered azithromycin sample.

TABLE 1

Stability of Non-Dihydrate Azithromycin in Suspension

| | Constituted | Storage Time | | Day 1 | 5 | 10 |
|---|---|---|---|---|---|---|
| Form G | Formulation II | 5° C. | % A | 72 | 75 | 78 |
| | | 30° C. | % A | 82 | 74 | 76 |
| | Bulk Drug | 5° C. | % A | 1 | 6 | 12 |
| | | 30° C. | % A | 3 | 26 | 73 |
| Form M | Formulation II | 5° C. | % A | 23 | 38 | 40 |
| | | 30° C. | % A | 28 | 36 | 62 |
| | Bulk Drug | 5° C. | % A | 0 | 0 | 0 |
| | | 30° C. | % A | 0 | 0 | 0 |
| Form N | Formulation II | 5° C. | % A | 24 | NA | 53 |
| | | 30° C. | % A | 28 | NA | 53 |
| | Bulk Drug | 5° C. | % A | 0 | NA | 0 |
| | | 30° C. | % A | 0 | NA | 0 |
| Form F | Formulation II | 5° C. | % A | 6 | NA | 27 |
| | | 30° C. | % A | 19 | NA | 31 |
| | Bulk Drug | 5° C. | % A | 0 | NA | 0 |
| | | 30° C. | % A | 0 | NA | 0 |
| Form J | Formulation II | 5° C. | % A | 0 | NA | 0 |
| | | 30° C. | % A | 0 | NA | 0 |
| | Bulk Drug | 5° C. | % A | 0 | NA | 0 |
| | | 30° C. | % A | 0 | NA | 0 |

NA = Not Analyzed

Table 1 shows that forms G, N, M and F converted to azithromycin dihydrate at much greater rates when formulated in POS formulation II suspensions as compared to bulk drug suspended in deionized water for each form. These data demonstrated that the choice of components for POS formulations is important for limiting dihydrate formation upon constitution and storage.

Form J, unlike forms G, M, N and F, did not exhibit a greater conversion rate to the dihydrate when incorporated into a suspension made using POS formulation II.

The stability of form G azithromycin was also evaluated for suspensions prepared from POS formulations I, II and III. The form G bulk drug substance contained <1% by weight of form A prior to formulation and constitution. These suspensions were constituted with 18 mls of water and stored for 1 and 10 days at 30° C. The observed conversion to the azithromycin dihydrate (form A) is provided in Table 2.

TABLE 2

Stability of Azithromycin Form G in Various Suspension Formulations

| Day | Formulation I (% Form A) | Formulation II (% Form A) | Formulation III (% Form A) |
|---|---|---|---|
| 1 | 0 | 84 | 27 |
| 10 | 0 | 91 | 52 |

This study demonstrated that the inclusion of various flavoring components in the azithromycin form G suspension resulted in significant conversion of form G to azithromycin dihydrate (form A). This study also demonstrated that azithromycin form G. in a suspension including sucrose and hydroxypropyl cellulose (HPC) and without any flavoring components (Formulation I), did not exhibit conversion to form A. This example also showed that the particular banana flavor used in the suspension could alter the rate of conversion to form A.

EXAMPLE 2

Effect of Individual Flavorings and Sucrose on Form Conversion

To evaluate a proposed excipient, the active dose of the azithromycin was suspended with the desired amount of potential excipient in a 0.1 M phosphate buffer system adjusted to a pH of 8.16. The buffer system was created by dissolving 13.738 g of $NaH_2PO_4 \cdot H_2O$ in 900 ml of water, adjusting the pH to 8.16 with sodium hydroxide, and diluting the solution to 1 liter with water. The sample, once constituted with buffer, was then stored at room temperature for the desired constituted product shelf-life. The azithromycin product was then isolated through filtration, and the resulting solid filtrate analyzed by a Solid-State Nuclear Magnetic Resonance method described previously that allows for quantitation of the dihydrate form present.

The effect of various individual flavoring components and of sucrose upon conversion of azithromycin form G to azithromycin dihydrate (form A), in suspensions, were evaluated as follows.

An 820 mg dose of form G azithromycin was weighed and mixed with 200 mg of each flavoring or sucrose. The mass of each flavoring, used in this test, was chosen to match that of the anticipated required amount for effective flavoring in the constituted POS. In this example, five flavorings, specifically artificial crème de vanilla, B&C banana, Trusil banana, Trusil cherry and artificial grape were investigated in addition to sucrose. Each of the binary samples were then constituted with 18 mls of pH=8.16 buffer and stored for 1, 5 and 10-days at room temperature.

A control suspension of azithromycin form G constituted with 18 mls of pH=8.16 buffer was run with each series of experiments using the same storage conditions. Upon completion of the constituted storage time period these samples were filtered to isolate drug product and analyzed using the SS-NMR method to quantify the amount of azithromycin dihydrate present.

The results of these studies are provided in the following Table 3.

TABLE 3

Effect of Flavorings and Sucrose On Conversion of Azithromycin Form G to Form A)

| Formulations | Constituted 1 day (Δ % Form A) | Constituted 5 days (Δ % Form A) | Constituted 10 days (Δ % Form A) |
|---|---|---|---|
| Artificial Crème de Vanilla Flavor | 0% | 4% | 30% |
| B&C Banana Flavor | 0% | 27% | AC |
| Trusil Banana Flavor | 32% | 57% | AC |
| Sucrose | 2% | 1% | 6% |
| Trusil Cherry Flavor | 32% | 75% | AC |
| Artificial Grape Flavor | 57% | 75% | AC |

AC means all converted to form A

As shown previously in Example 1, azithromycin form G, in combination with only water, experienced significant conversion to form A over the 10-day constitution interval. Further, when combined with a flavoring, such as Artificial Crème de vanilla, artificial grape, Trusil cherry, B&C banana or Trusil banana, the rate of conversion substantially increased.

Thus, this test shows that these five flavorings need to be stabilized for use in oral suspension formulations of azithromycin form G with a 5–10 day constituted shelf-life. However, suspensions with Artificial Creme de vanilla and B&C banana flavorings did not exhibit conversion to azithromycin dihydrate (form A) during the first day after constitution.

Further, the presence of sucrose, without flavoring, appears to have stabilized the azithromycin form G in a constituted suspension such that only minimal conversion to form A was observed over the 10-day period.

This example demonstrated a simple method for choosing suitable excipients for non-dihydrate azithromycin oral suspensions that will minimize form conversion.

EXAMPLE 3

Identification of Components of Flavorings which Promote Azithromycin Form Conversion In Example 1, it was shown that, when a non-dihydrate azithromycin was constituted in a flavored suspension, suitable for use as an oral suspension dosage form, azithromycin form conversion was exhibited. Further, the high conversion rate produced in suspensions containing Trusil artificial banana, as compared to B&C Banana, demonstrated that Trusil artificial banana contains a greater amount of conversion enhancers, or more efficient conversion enhancers, than does B&C Banana.

To evaluate the effects of various components of suspension flavorings on non-dihydrate azithromycin form conversion, the major components of Artificial Crème de vanilla, Trusil cherry, B&C banana or Trusil banana in example 2 were identified and quantified using Gas Chromatography. Sucrose was also analyzed.

Samples were prepared for analysis by weighing 150 mg of each excipient into a 20 ml headspace vial (Tekmar Corporation; Mason, Ohio), diluting with 2 ml of N,N-Dimethylacetamide (DMAC) and swirled on a vortex mixer in order to fully dissolve the sample. Three mls of saline diluent (0.25 g/ml sodium chloride solution) were then added to the sample. The sample headspace vial was sealed with a Teflon-lined septum and a crimp cap. The sample was then swirled briefly to mix.

The samples were analyzed using an HP 7694 headspace autosampler system and an HP 6850 series gas chromatograph equipped with a flame ionization detector, with split injection capability for capillary column operation (Hewlett-Packard; Palo Alto, Calif.) and a 30 meter×0.32 mm I.D. fused silica capillary column with a DB-624 stationary phase (J&W Scientific; Rancho Cordova, Calif.). The instrument parameters are described in Tables 4 and 5. The results of these analyses are provided in Tables 6 and 7.

TABLE 4

Headspace Autosampler Parameters

| Parameter | Setting/value |
| --- | --- |
| Sample Temperature | 105° C. |
| Heating Time | 60 minutes |
| Vial Pressurization | 12 PSI with Helium |
| Injection Volume | 2 ml |
| Sample Pressure | 6 PSI |
| Transfer Line Temperature | 115° C. |

TABLE 5

Gas Chromatographic System Parameters

| Parameter | Setting/value |
| --- | --- |
| Oven Temperature (program) | 40° C. for 5 min. (ramp 2° C./min.) 90° C. for 0 min. (ramp 30° C./min.) 225° C. for 2 min. Total time = 36.5 minutes |
| Column Flow | 1.6 ml/min. helium |
| Split Flow | 47 ml/min. |
| Split Ratio | 30:1 |
| Detector Temperature (FID) | 260° C. |
| Attenuation | Set to Maximum Sensitivity |
| Integration mode | Peak areas |

TABLE 6

Specific Components in Flavorings and Sucrose
(Values reported as % w/w of Excipient)

|  | Trusil Art. Banana | Trusil Art. Cherry | B&C Art. Banana | Art. Crème de Vanilla | Sucrose |
| --- | --- | --- | --- | --- | --- |
| 3-Methyl-butyl acetate | 7.5% | 0.74% | 1.8% | <0.01% | <0.01% |
| 2-Methyl-butyl acetate | 1.2% | 0.15% | 0.43% | <0.01% | <0.01% |
| 3-Methyl-1-butanol | 0.19% | <0.01% | <0.01% | <0.01% | <0.01% |
| Isoamyl Isovalerate | 0.13% | 0.39% | <0.01% | <0.01% | <0.01% |
| Benzaldehyde | <0.01% | 8.8% | <0.01% | <0.01% | <0.01% |
| Ethyl acetate | 0.01% | 2.8% | <0.01% | <0.01% | <0.01% |
| Ethyl ester propanoic acid | 0.01% | <0.01% | <0.01% | <0.01% | <0.01% |

TABLE 7

Volatile Components in Flavorings and Sucrose

| Excipient | Number of Volatile Organics | Amount of Volatile Organics (% w/w of excipient) |
| --- | --- | --- |
| Trusil Art. Banana | 22 | 9.7 |
| Trusil Art. Cherry | 15 | 16.8 |
| B&C Art. Banana | 9 | 3.2 |

TABLE 7-continued

Volatile Components in Flavorings and Sucrose

| Excipient | Number of Volatile Organics | Amount of Volatile Organics (% w/w of excipient) |
| --- | --- | --- |
| Art. Crème de Vanilla | 4 | ~0.1 |
| Sucrose | 1 | ~0.1 |

The data showed that both the sucrose and vanilla flavorings contain only trace amounts of volatile organics that could result in the azithromycin form conversion. This correlated well to the lower conversion rate of these two formulation components. The Trusil cherry and banana flavorings, however, appeared to have significant amounts of volatile organics that may be responsible for the greater conversion enhancing behavior of these excipients.

Standards of these identified solvent components were then used to investigate the source of the stability problem introduced by these flavorings. The estimated concentration of each solvent in a constituted POS was calculated based on the GC-MS quantification of the specified solvent in the flavorings. Aqueous solutions of each solvent/component were then created at these concentrations and 18 mls of each solvent-solution was used to constitute an unflavored POS formulation I sample using form G. The constituted drug suspensions were stored at room temperature for 24-hours, before being filtered and analyzed by SS-NMR for quantification of azithromycin form change over this interval. POS formulations I and II were constituted with 18 mls of water and stored identically to serve as controls for this experiment. The results of this investigation can be seen in Table 8, below.

TABLE 8

Effects of Flavoring Components Upon Azithromycin Form G Conversion

| Form G POS Formulation | Constitution Medium (18 mL) | % Form A |
| --- | --- | --- |
| Formulation II | Water | 71 |
| Formulation I | Water | 0 |
| Formulation I | 0.197 mg/ml ethyl acetate | 0 |
| Formulation I | 0.002 mg/ml ethyl ester propanoic acid | 0 |
| Formulation I | 0.025 mg/ml 3-methyl-1-butanol | 0 |
| Formulation I | 0.815 mg/ml 3-methyl-butyl acetate | 2 |
| Formulation I | 0.144 mg/ml 2-methyl-butyl acetate | 0 |
| Formulation I | 0.587 mg/ml benzaldehyde | 0 |
| Formulation I | 0.043 mg/ml isoamyl isovalerate | 13 |
| Formulation I | 0.785 mg/ml 3-methyl-butyl acetate + 0.562 mg/ml benzaldehyde | 11 |

When constituted with water, form G azithromycin in POS formulation II demonstrated approximately 71% conversion to azithromycin dihydrate. POS formulation I which is POS formulation II without the cherry, Trusil banana and vanilla flavorings, had no conversion to the azithromycin dihydrate when constituted with water. The constitution of POS formulation I with 3-methyl-butyl acetate and isoamyl isovalerate solutions, instead of water, exhibited an increased conversion to azithromycin dihydrate. As a result of this observation it is evident that an azithromycin POS formulation will be more stable if the levels of these organic components are minimized, or absent from the constituted POS all together. Flavorings should be chosen which do not contain these organic components for optimal POS stability. Furthermore, the stability of a constituted POS formulation can be improved by substituting flavorings that contain small amounts of these organic components for those in the formulation that have large amounts of these organic components.

It was also demonstrated that these organic components may not enhance the conversion in an independent manner. Combinations of organic components, as demonstrated through constitution with a 0.785 mg/ml 3-methyl-butyl acetate and 0.562 mg/ml benzaldehyde solution, may also interact to further facilitate the formation of the dihydrate species as compared to the effect of individual isolated components. For this reason it is beneficial not only to avoid such combinations of components through careful flavoring choices, but also to choose flavorings with the least amount of organic components in order to minimize the probability of observing such a phenomenon.

An identical test was also performed using form F azithromycin. The calculated solvent levels were again used to create solutions of these single components in water and used to constitute samples of POS formulation I using form F. The constituted drug suspensions were stored at room temperature for 24-hours, before being filtered and analyzed by SS-NMR for quantification of azithromycin form change over this interval. POS formulation II was constituted with water and stored identically to serve as a control for this experiment. The design and results of this investigation can be seen in Table 9.

TABLE 9

Effects of Flavoring Components Upon Azithromycin Form F Conversion

| Form F POS Formulation | Constitution Medium (18 mL) | SS-NMR Evaluation after 24 hrs constitution | | |
|---|---|---|---|---|
| | | % F | % A | % G |
| Formulation II | Water | 0 | 59 | 41 |
| Formulation I | 0.922 mg/ml 3-methyl-butyl acetate | 0 | 0 | 0 |
| Formulation I | 0.0577 mg/ml benzaldehyde | 0 | 0 | 0 |
| Formulation I | 1.666 mg/ml 3-methyl-butyl acetate | 0 | 5 | 0 |
| Formulation I | 0.922 mg/ml 3-methyl-butyl acetate + 0.0577 mg/ml benzaldehyde | 0 | 6 | 0 |

Form F also demonstrated form conversion in the presence of organic flavoring components including 3-methyl-butyl acetate, either separately or in combination with benzaldehyde. It was also observed during this experiment that form F azithromycin had a tendency to convert to form G or other forms.

EXAMPLE 4

Stabilization by Addition of Surface Active Components

This example demonstrates that when excipients, which can decrease surface tension, such as anionic and non-ionic surfactants and surface active polymers, are incorporated into a POS formulation, the non-dihydrate azithromycin in suspension was stabilized against conversion.

Forms F and M azithromycin were formulated into POS formulation II. A series of surfactants and polymers were then added to these formulations and the resulting samples constituted with 18mls of water. After 24-hours of room temperature storage the samples were filtered and analyzed by SS-NMR for quantitation of dihydrate species present. The data are presented in Tables 10 and 11 and are given as the percent that is converted to form A relative to a control sample. Thus, additives with conversion values greater than 100% show that more non-dihydrate azithromycin was converted to form A than in the control sample while values less than 100% show that the additive is decreasing the conversion to form A compared to the control sample. The control sample consisted of non-dihydrate azithromycin form F or form M in formulation II, which was shown to promote conversion to azithromycin dihydrate (form A). The control sample was constituted with water, stored and analyzed identically to the additive samples as described above.

TABLE 10

Addition of Polymeric and Surfactant Components to Slow Form F Conversion

| Additive | Additive Level (% w/v) | Surface Tension (dyne/cm) | % Conversion to Form A Relative to the Control Sample |
|---|---|---|---|
| Sodium Dioctyl Sulfosuccinate | 1 | 25.6[1] | 0 |
| Sodium Lauryl Sulfate | 1 | 35.8[2] | 0 |
| Hydroxypropyl Methylcellulose Acetate Succinate | 1 | 43.7[3] | 23 |
| Hydroxypropyl Methylcellulose | 0.2 | 47.1[2] | 43 |
| Carboxymethylcellulose Sodium | 1 | 70.9[2] | 106 |
| Cellulose Acetate Phthalate | 1.5 | 51.3[3] | 136 |
| Polyvinylpyrrolidone | 1 | 68.3[2] | 111 |

[1]Literature Value (Johnson, Barbara A., Kreuter, Jorg and Zografi, George, "Effects of Surfactants and Polymers on Advancing and Receding Contact Angles" Colloids and Surfaces, 17 (1986) 325–342.)
[2]Surface tension of an aqueous solution of the polymer at the concentration used in the suspension determined with a Kruss Tensiometer using the Wilhemy plate method at room temperature.
[3]Surface tension of the saturated aqueous solution of the polymer determined with a Kruss Tensiometer using the Wilhemy plate method at room temperature.

TABLE 11

Addition of Polymeric and Surfactant Components to Slow Form M Conversion

| Additive | Additive Level (% w/v) | Surface Tension (dyne/cm) | % Conversion to Form A Relative to the Control Sample |
|---|---|---|---|
| Sodium Dioctyl Sulfosuccinate | 1 | 25.6[1] | 0 |
| Sodium Lauryl Sulfate | 1 | 35.8[2] | 0 |
| Igepal ® CO-630 | 1 | 32[3] | 8 |
| Pluronic ® F68NF | 1 | 43.2[1] | 10 |
| Hydroxypropyl Cellulose | 0.3 | 42[1] | 72 |

TABLE 11-continued

Addition of Polymeric and Surfactant Components to Slow Form M Conversion

| Additive | Additive Level (% w/v) | Surface Tension (dyne/cm) | % Conversion to Form A Relative to the Control Sample |
|---|---|---|---|
| Hydroxypropyl Methylcellulose | 0.4 | 47[1] | 97 |
| Polyvinylpyrrolidone | 1 | 68.3[2] | 107 |

[1]Literature Value (Johnson, Barbara A., Kreuter, Jorg and Zografi, George, "Effects of Surfactants and Polymers on Advancing and Receding Contact Angles" Colloids and Surfaces, 17 (1986) 325–342.)
[2]Surface tension of an aqueous solution of the polymer at the concentration used in the suspension determined with a Kruss Tensiometer using the Wilhemy plate method at room temperature.
[3]GAF Chemicals Corp., Technical Bulletin 2303-015R2 (1986)

This example showed that additives which are surface active such as hydroxypropyl methylcellulose, hydroxypropyl methylcellulose acetate succinate, sodium lauryl sulfate and sodium dioctyl sulfosuccinate are effective in slowing the conversion of form F to the dihydrate form. The anionic surfactants, sodium lauryl sulfate and sodium dioctyl sulfosuccinate, are also shown as effective for inhibiting conversion of a second non-dihydrate azithromycin form (form M). The cellulosic polymers, hydroxypropyl cellulose and hydroxypropyl methylcellulose, and the polyoxyethylene-polyoxypropylene copolymer Pluronic® F68NF and the nonionic surfactant nonylphenoxy polyoxyethylene Igepal® CO-630 were also found to slow the conversion of non-dihydrate azithromycin form M. The effectiveness of these additives is related to their surface activity as shown in Tables 10 and 11.

EXAMPLE 5

Effect of Viscosity on Form Conversion

The effects of suspension viscosity on non-dihydrate azithromycin form conversion were evaluated.

Viscosifying agents were incorporated into POS formulations in the absence of conversion enhancers, such as flavoring components. Specifically, a series of viscous media was prepared by dissolving various amounts of either sucrose or sorbitol in a 0.22 M phosphate buffer solution. Each solution was then adjusted with sodium hydroxide to bring the mixture to a pH of 7.8. The viscosity of each constitution media was measured using a Brookfield digital viscometer (model DV-II) equipped with a 13R sample chamber and #18 spindle. A heating jacket was also used to maintain the 8 ml sample volume to a temperature of 21° C. during measurements. 18 mls of each viscous media were then used to constitute 820 mg of form G azithromycin. The resulting suspensions were stored at room temperature for both 5 and 10-days. Upon conclusion of the storage time period the constituted samples were filtered and analyzed by SS-NMR for quantitation of dihydrate species present. The form conversion observed is reported in Tables 12 and 13.

TABLE 12

Effect of Sucrose Vehicle Viscosity on Conversion in Flavoring-free Form G Azithromycin Suspensions

| Formulation | Constitution Media (mg/ml sucrose solution) | Constitution Media Viscosity (cP) | 5-day Storage (% Form A) | 10-day Storage (% Form A) |
|---|---|---|---|---|
| Form G Only | 1.8 | 105.0 | 0 | 0 |
| Form G Only | 1.4 | 41.7 | 1 | 3 |
| Form G Only | 1.1 | 20.2 | 5 | 6 |
| Form G Only | 0.8 | 10.2 | 5 | 12 |
| Form G Only | 0.0 | 1.2 | 20 | 55 |

TABLE 13

Effect of Sorbitol Vehicle Viscosity on Conversion in Flavoring-free Form G Azithromycin Suspensions

| Formulation | Constitution Media (mg/ml sorbitol solution) | Constitution Media Viscosity (cP) | 5-day Storage (% Form A) | 10-day Storage (% Form A) |
|---|---|---|---|---|
| Form G Only | 2.04 | 130.9 | 0 | 0 |
| Form G Only | 1.54 | 21.0 | 0 | 0 |
| Form G Only | 1.02 | 3.4 | 7 | 7 |
| Form G Only | 0.0 | ~1 | 35 | 100 |

As shown above, in the absence of a conversion enhancer, such as the Trusil Banana flavoring, the constituted suspension of azithromycin form G demonstrated an increased stability against conversion with increasing suspension viscosity. As a result, the addition of viscosifying agents, such as sugars, hydric alcohols and/or polymeric substances, are advantageous for creating stable azithromycin drug suspensions not having flavoring components. Analysis of the data allows one to formulate an azithromycin POS with viscosifying agents that is resistant to conversion over the desired product shelf-life.

In Table 14, this example further demonstrated that conversion to the dihydrate in a constituted POS was minimized by the omission of viscosifying agents for POS formulations that contain a conversion enhancer.

Powder blends, comprising 820 mg azithromycin form G and 200 mg Trusil Artificial Banana flavoring, were formed. 18 mls of various sucrose solutions, as the constitution media, were added to each sample and the resulting suspensions were then stored for 24-hours at room temperature before being filtered and analyzed by SS-NMR to quantify the amount of dihydrate (form A) present.

TABLE 14

Effect of Viscosity on Dihydrate Formation in a Flavored Form G Azithromycin Suspension

| Formulation | Constitution Media (mg/ml sucrose solution) | Constitution Media Viscosity (cP) | 24-hour Storage (% Form A) |
|---|---|---|---|
| Form G + Trusil Banana Flavor | 1.8 | 105.0 | 68 |
| Form G + Trusil Banana Flavor | 1.4 | 41.7 | 65 |

TABLE 14-continued

Effect of Viscosity on Dihydrate Formation in a Flavored Form G Azithromycin Suspension

| Formulation | Constitution Media (mg/ml sucrose solution) | Constitution Media Viscosity (cP) | 24-hour Storage (% Form A) |
|---|---|---|---|
| Form G + Trusil Banana Flavor | 1.1 | 20.2 | 65 |
| Form G + Trusil Banana Flavor | 0.8 | 10.2 | 70 |
| Form G + Trusil Banana Flavor | 0.0 | 1.2 | 35 |

These data indicate that higher viscosity suspensions, which contain a conversion enhancer such as the Trusil Banana flavoring component, have higher rates of conversion of azithromycin form G to azithromycin dihydrate. Thus, to minimize conversion of azithromycin form G in a flavored suspension, a decrease of constituted POS viscosity is indicated, either through the reduction or omission of viscosifying agents in the formulation. Examples of suitable sweetening alternatives to sucrose that do not viscosify the constituted POS include saccharin, aspartame, acesulfame potassium, thaumatin, and monelin.

We claim:

1. A powder for oral suspension, comprising:
   a) a n-propanol solvate of non-dihydrate azithromycin; and
   b) at least one pharmaceutically acceptable excipient.

2. The powder for oral suspension of claim 2 wherein said n-propanol solvate of azithromycin is azithromycin form J.

3. An oral suspension, comprising:
   a) a n-propanol solvate of non-dihydrate azithromycin; and
   b) an aqueous vehicle.

4. The oral suspension of claim 3 wherein said n-propanol solvate of azithromycin is azithromycin form J.

* * * * *